United States Patent
Detor et al.

(10) Patent No.: US 10,605,719 B2
(45) Date of Patent: Mar. 31, 2020

(54) EQUIPMENT CONDITION-BASED CORROSION LIFE MONITORING SYSTEM AND METHOD

(71) Applicant: General Electric Company, Schenectady, NY (US)

(72) Inventors: Andrew Joseph Detor, Burnt Hills, NY (US); Bernard Patrick Bewlay, Niskayuna, NY (US); Monica Soare, Niskayuna, NY (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 155 days.

(21) Appl. No.: 15/617,736

(22) Filed: Jun. 8, 2017

(65) Prior Publication Data

US 2018/0356334 A1 Dec. 13, 2018

(51) Int. Cl.
| | | |
|---|---|---|
| *G01N 17/04* | (2006.01) | |
| *G01N 17/00* | (2006.01) | |
| *G05B 23/02* | (2006.01) | |
| *G01B 11/02* | (2006.01) | |
| *G01B 21/16* | (2006.01) | |
| *G01M 15/14* | (2006.01) | |

(52) U.S. Cl.
CPC ............. *G01N 17/04* (2013.01); *G01B 11/02* (2013.01); *G01B 21/16* (2013.01); *G01N 17/006* (2013.01); *G05B 23/0283* (2013.01); *G01M 15/14* (2013.01)

(58) Field of Classification Search
CPC ...... G01N 17/04; G01N 17/006; G01N 21/88; G01B 11/02; G01B 21/16; G05B 23/0283
See application file for complete search history.

(56) References Cited

U.S. PATENT DOCUMENTS

| | | | |
|---|---|---|---|
| 5,315,234 A | 5/1994 | Sutton, Jr. et al. | |
| 5,345,514 A | 9/1994 | Mahdavieh et al. | |
| 6,792,357 B2 | 9/2004 | Menon et al. | |
| 7,317,992 B2 | 1/2008 | Fascinato et al. | |
| 7,609,874 B2* | 10/2009 | Eswara | G06K 9/00 |
| | | | 382/149 |
| 7,689,003 B2 | 3/2010 | Shannon et al. | |

(Continued)

OTHER PUBLICATIONS

Gao et al., "Determining the Remaining Strength of Pitting Corrosion in Corroded Pipelines with API579 Criterion," 2011, 2011 International Conference on Computational and Information Sciences, pp. 687-690.*

(Continued)

*Primary Examiner* — Jennifer E Simmons
*Assistant Examiner* — Leo T Hinze
(74) *Attorney, Agent, or Firm* — Christopher R. Carroll; The Small Patent Law Group LLC

(57) ABSTRACT

An analysis controller determines multi-dimensional characteristics of one or more corrosion pits in equipment. These characteristics can include depths, widths, and/or aspect ratios of the corrosion pits. The controller also determines one or more stresses on the equipment based on the characteristics of the corrosion that are determined. The analysis controller also generates a control signal to implement one or more remedial actions to one or more of remove the one or more corrosion pits, repair the equipment, or restrict operation of the equipment based on the one or more stresses that are determined.

20 Claims, 5 Drawing Sheets

(56) References Cited

U.S. PATENT DOCUMENTS

| | | | |
|---|---|---|---|
| 7,925,454 B1 | 4/2011 | Narcus | |
| 8,060,835 B2 * | 11/2011 | Newcomer | G06T 19/20 382/149 |
| 8,209,839 B1 | 7/2012 | Brostmeyer et al. | |
| 8,240,042 B2 | 8/2012 | Williams et al. | |
| 8,428,910 B2 | 4/2013 | Papadimitriou et al. | |
| 8,457,906 B2 * | 6/2013 | Ramachandran | G01N 17/006 702/34 |
| 8,818,078 B2 | 8/2014 | Telfer et al. | |
| 2006/0288756 A1 * | 12/2006 | De Meurechy | G01N 17/006 73/1.01 |
| 2016/0069789 A1 | 3/2016 | Pensado et al. | |
| 2016/0102554 A1 | 4/2016 | Cornell | |
| 2016/0196643 A1 | 7/2016 | Bendall | |

OTHER PUBLICATIONS

4D Technology Corporation; "The New 4D InSpec Surface Gauge is here!", 4D InSpec Surface Gauge, https://www.4dinspec.com/, 2017, (2 pages).
4D Technology Corporation; "4D InSpec Surface Gauge", 4D InSpec Surface Gauge, www.4DTechnology.com, 2016. (2 pages).
4D Technology Corporation; "4D InSpec FAQ (Frequently Asked Questions)", https://www.4dinspec.com/products/4d-inspec-faq/, 4D InSpec Surface Gauge, 2017, (7 pages).
4D Technology Corporation; "4D InSpec Applications", https://www.4dinspec.com/applications/, 4D InSpec Surface Gauge, 2017, (5 pages).
4D Technology Corporation; "4D InSpec Options", https://www.4dinspec.com/products/options/, 4D InSpec Surface Gauge, 2017, (5 pages).
4D Technology Corporation; "Revolutionary new measurement tool for the shop floor.", https://www.4dinspec.com/products/4d-inspec/, 4D InSpec Surface Gauge, 2017, (4 pages).
4D Technology Corporation; "Powerful, easy to use analysis for 4D InSpec.",https://www.4dinspec.com/products/4d-inspec-software/, 4D InSpec Surface Gauge, 2017, (6 pages).
Cunha, D.J.S., et al., "Fatigue analysis of corroded pipelines subjected to pressure and temperature loadings," International Journal of Pressure Vessels and Piping, vol. 113, pp. 15-24 (Nov. 7, 2013).
Filho, A.J.E., et al., "On the failure pressure of pipelines containing wall reduction and isolated pit corrosion defects," Computers and Structures, vol. 132, pp. 22-33 (Feb. 2014).
Gao, S.W., et al.,"Determining the Remaining Strength of Pitting Corrosion in Corroded Pipelines with API579 Criterion," International Conference on Computational and Information Sciences, pp. 687-690 (Oct. 21, 2011).
Sriraman, M.R. and Pidaparti, R.M., "Life Prediction of Aircraft Aluminum Subjected to Pitting Corrosion Under Fatigue Conditions," Journal of Aircraft, vol. 46, No. 4, pp. 1253-1259 (Jul.-Aug. 2009).
Partial Search Report and Opinion issued in connection with corresponding EP Application No. 18176456.4 dated Nov. 22, 2018.
Office Action dated Jun. 28, 2019 for corresponding CA Application No. 3,006,122.
Extended Search Report dated Mar. 1, 2019 for corresponding EP Application No. 18176456.4.

* cited by examiner

EQUIPMENT CONDITION-BASED CORROSION LIFE MONITORING SYSTEM AND METHOD

FIELD

The subject matter described herein relates to monitoring corrosion of equipment, such as turbine engines or other equipment.

BACKGROUND

Equipment that includes metal components can corrode over time. The corrosion can develop pitting in the equipment, which eventually can lead to cracks in the equipment and eventual failure of the equipment. Equipment may be scheduled for periodic inspection to check on the existence and/or progression of corrosion. But, this periodic inspection of corrosion may only examine the propagation of cracks and/or may only measure a single corrosion pit, and not examine other aspect of corrosion. As a result, predictions of how much longer the equipment can continue to safely operate (e.g., the remaining useful service life of the equipment) may be inaccurate.

BRIEF DESCRIPTION

In one embodiment, a system includes an analysis controller configured to determine multi-dimensional characteristics of one or more corrosion pits in equipment and to determine one or more stresses on the equipment based on the characteristics of the corrosion that are determined. The analysis controller also is configured to generate a control signal to implement one or more remedial actions to one or more of remove the one or more corrosion pits, repair the equipment, or restrict operation of the equipment based on the one or more stresses that are determined.

In one embodiment, a method includes optically determining multi-dimensional characteristics of one or more corrosion pits in equipment, determining one or more stresses on the equipment based on the multi-dimensional characteristics of the one or more corrosion pits that are determined, and implementing one or more remedial actions to one or more of remove the one or more corrosion pits, repair the equipment, or restrict operation of the equipment based on the one or more stresses that are determined.

In one embodiment, a system includes an analysis controller configured to determine one or more multi-dimensional characteristics of corrosion pits in equipment and to determine one or more operational characteristics of the equipment. The analysis controller also is configured to determine one or more stresses on the equipment based on the one or more multi-dimensional characteristics of the corrosion that are determined and based on the one or more operational characteristics. The analysis controller also is configured to generate a control signal to implement one or more remedial actions to one or more of remove the corrosion pits, repair the equipment, or de-rate operation of the equipment based on the one or more stresses that are determined.

BRIEF DESCRIPTION OF THE DRAWINGS

The present inventive subject matter will be better understood from reading the following description of non-limiting embodiments, with reference to the attached drawings, wherein below.

DETAILED DESCRIPTION

Figure 1:
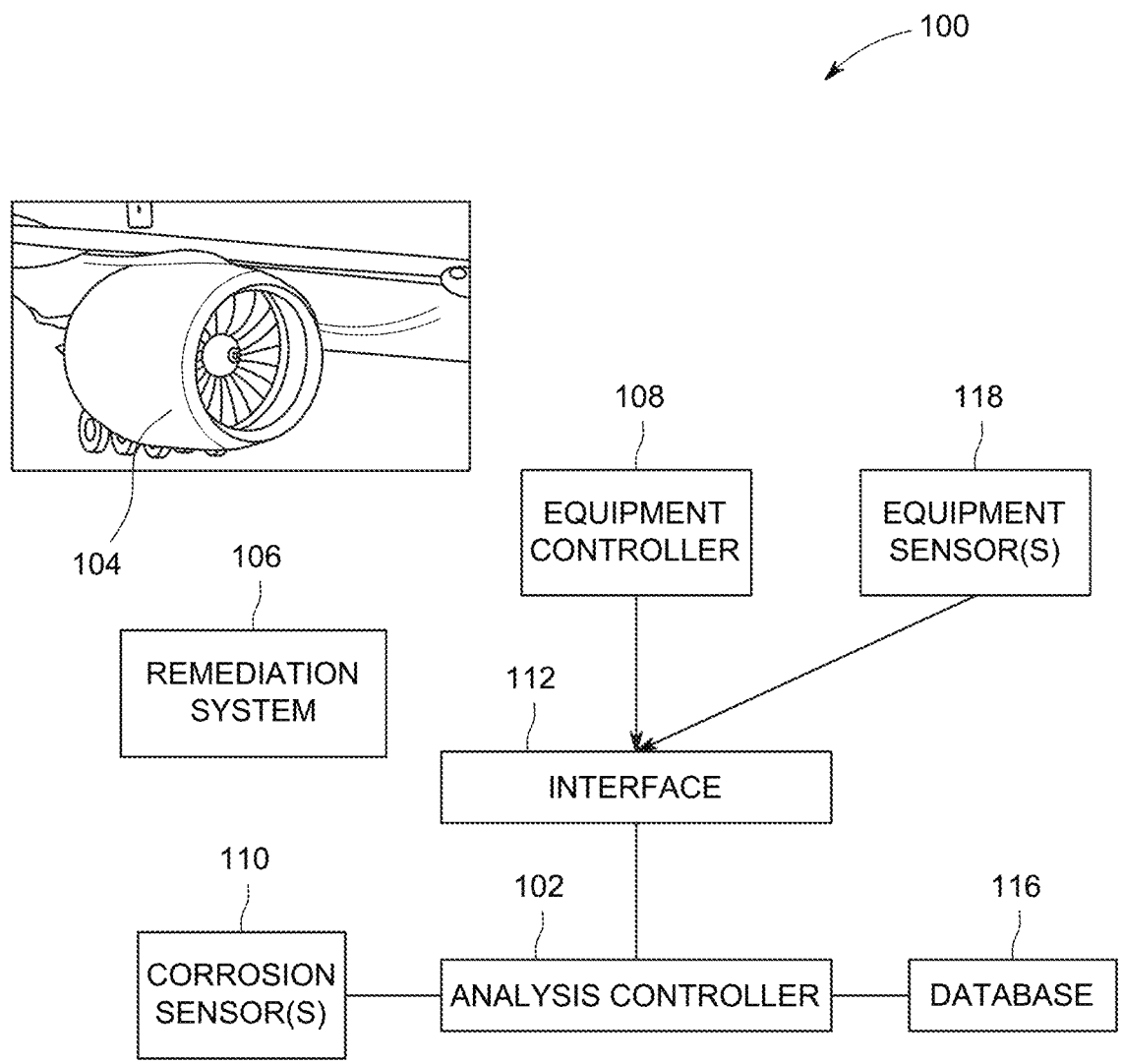
FIG. 1 illustrates one embodiment of a corrosion monitoring system.

One or more embodiments of the inventive subject matter described herein provide systems and methods that monitor corrosion of equipment and, based on the corrosion that is monitored, determine a predicted remaining useful service life of the equipment. While the description herein focuses on predicting the remaining useful service life of engine turbines, the systems and methods can be used to predict the remaining useful service life of other types of equipment, such as other vehicle components, bridges, rails, or the like. The prediction of the remaining useful service life of equipment can be referred to as lifting the equipment. The predicted remaining useful service life can represent an amount of time that the system or method predict that the equipment can continue to be operational before failing or otherwise being unable to function.

The systems and methods can apply an analytic based equipment corrosion life monitor in conjunction with optical measurements of corrosion pits in the equipment. The systems and methods can use multi-dimensional surface information regarding the corrosion pit population (such as a depth, width, and/or aspect ratio of one or more corrosion pits) to quantify stress concentrations associated with a field of corrosion pits, as well as a resulting modified crack initiation life. For example, the systems and methods can determine the corrosion pit aspect ratio and corrosion pit locations to quantify stress concentration and crack initiation life in the equipment. The aspect ratio for a corrosion pit can be the ratio of the width of the pit to the depth of the pit. The corrosion pit locations can be relative locations of the pits to each other (e.g., expressed as a number of pits per unit area on the equipment, an average or median distance between corrosion pits, etc.) and/or absolute locations of the pits (e.g., distances or vectors of the pits from the same or common location).

The systems and methods optionally also can employ corrosion pit population data to quantify the impact of multiple corrosion pit interactions on the remaining useful service life of the equipment. For example, closer corrosion pits and/or greater numbers of corrosion pits that are close to each other are more likely to result in generation of a crack in the equipment compared to corrosion pits that are farther apart and/or a smaller number of corrosion pits that are close to each other. The systems and methods optionally can predict growth of corrosion pits based on operating conditions of the equipment. This information also can impact the predicted remaining useful service life of the equipment.

With respect to a turbine engine or another type of engine, the systems and methods can operate by analyzing engine data including engine operating parameters, analyzing vehicle routes (e.g., flight routes including inter-city pairs, or groups of locations between which the engine traveled on the vehicle), analyzing environmental exposure of the engine for the routes or missions, and identifying a level of exposure of the engine to corrosion damage. The engine can be inspected for corrosion damage at an identified usage point. Characteristics of the surface corrosion pit field in the engine can be measured, such as the number of corrosion pits, locations of the corrosion pits, density of corrosion pits, sizes (e.g., aspect ratios) of the corrosion pits, etc.

Using this corrosion data, a stress analyses of a part of the engine or equipment that has experienced corrosion damage is performed at the operating mission conditions, such as operating speeds, temperatures, etc. The effect of the corrosion pits on stresses in the equipment is determined, and areas where predicted stress indicates a risk of crack initiation are identified. The stress increase generated by individual corrosion pits is determined. The stress increase generated by the combined effect of adjacent or neighboring corrosion pits in the pit field is determined using the stress analysis. The residual life of the part or engine is determined based on the engine operation or exposure, the measurements of the corrosion pits, and/or the component analyses.

The ability to monitor corrosion degradation based on equipment data and environmental exposure is becoming increasing important, and provides one or more technical effects. Defining the residual life of components using corrosion measurements, performing stress analyses, and establishing residual component life provides beneficial information on determining how or when to take equipment out of service for replacement and/or repair. For example, taking a turbine engine of an airplane out of service can result in significantly long downtimes for the airplane and can be a costly endeavor. Unnecessarily taking the engine out of service before service is needed can result in wasted time and/or cost. Additionally, performing proactive service on the corrosion on an engine based on the predicted remaining useful service life can extend the life of the engine relative to performing the service only on a periodic basis.

FIG. 1 illustrates one embodiment of a corrosion monitoring system 100. The system 100 includes an analysis controller 102 that monitors equipment performance parameters and predicts corrosion degradation of equipment 104, such as a turbine engine of an aircraft (or another type of engine, another engine for another type of vehicle, or another type of equipment other than an engine). Responsive to predicting corrosion degradation, the analysis controller 102 can automatically implement one or more responsive or remediation actions. These actions can be performed without removing the equipment 104 from the powered system to which the equipment 104 is coupled, such as the aircraft or wing of the aircraft. With respect to equipment 104 that is stationary, the actions can be performed without removing the equipment 104 from a surface to which the equipment 104 is mounted. For example, for industrial gas turbine engines mounted to surfaces, the actions can be implemented without removing the engines from the surfaces.

A remediation system 106 represents one or more hardware components that change a state of the equipment 104 to reduce the effect of further corrosion. For example, the remediation system 106 can include a cleaning system that applies water, air, or the like, to remove corrosive species from the equipment 104. Optionally, the remediation system 106 can be a scheduling system that changes a schedule of the vehicle to avoid city-to-city flight paths that involve exposure to dust that causes hot corrosion. As another example, a remediation action performed and/or scheduled by the system 106 can include replacing a filter or filter system on the equipment 104, such as a filter that removes particulates from air directed into the equipment 104.

As another example, the remediation system 106 can communicate with an equipment controller 108 that controls operation of the equipment 104. The equipment controller 108 can modify operating parameters of the equipment 104, such as to de-rate the equipment 104, to reduce an upper limit on an operating temperature of the equipment 104, and/or to otherwise reduce stresses of the equipment 104 to reduce the rate of corrosion. De-rating the equipment 104 can include lowering an upper limit on operation of the equipment 104, such as lowering the amount of horsepower that can be generated by an engine. The remediation system 106 can include a spraying device that adds coatings to the equipment 104, including corrosion mitigation coatings.

The analysis controller 102 and/or equipment controller 108 represent hardware circuitry that includes and/or is connected with one or more processors (e.g., one or more microprocessors, field programmable gate arrays, and/or integrated circuits) that perform the associated operations described herein. Optionally, the analysis controller 102 and/or equipment controller 108 can include one or more processors (e.g. a controller, microprocessor, microcontroller, digital signal processor, etc.), one or more memories, one or more input/output subsystems, one or more laptop computers, one or more mobile devices (e.g., a tablet computer, smart phone, body-mounted device or wearable device, etc.), one or more servers, one or more enterprise computer systems, one or more networks of computers, etc. In one embodiment, the equipment controller 108 includes a full authority digital engine controller (FADEC), a component thereof, or as a separate module in communication with the FADEC (e.g., via one or more electronic communication links or networks). In some embodiments, the equipment controller 108 monitors a range of equipment characteristics, such as the frequency of data acquisition and communication with the analysis controller 102.

The controllers 102, 108 can communicate with each other via one or more networks. The network(s) may be, for example, a cellular network, a local area network, a wide area network (e.g., Wi-Fi), a cloud, a virtual personal network (e.g., VPN), a cloud, an Ethernet network, and/or a public network such as the Internet. The controllers 102, 108 can include and/or communicate with each other via communication subsystems. The communication subsystems may enable shorter-range wireless communications between the controllers 102, 108 using, for example, BLUETOOTH and/or other technology. The communication subsystems may include one or more optical, wired and/or wireless network interface subsystems, cards, adapters, or other devices, as may be needed pursuant to the specifications and/or design of the controllers 102, 108.

One or more corrosion sensors 110 can optically measure characteristics of corrosion in or on the equipment 104. In one embodiment, the corrosion sensor 110 includes an optical sensor that measures multi-dimensional information on corrosion in the equipment. This information can include locations and/or sizes of the corrosion pits in the equipment 104. The corrosion sensor 110 can include a structured light sensor that generates several points of light that are reflected off the equipment 104 and that measures reflection of the points of light. Based on changes in the emitted and detected points of light, the corrosion sensor 110 can detect interruptions in smooth surfaces of the equipment 104.

The presence of a corrosion pit can introduce changes in the reflection of the light when compared with the absence of a corrosion pit. For example, points of light that are a designated distance apart from each other when emitted from the sensor 110 can appear or be reflected toward the sensor 110 a different distance (e.g., the reflected points of light can be closer together or father apart) when the light reflects off a corrosion pit. This can be used by the sensor 110 and/or controller 102 to determine the location of the corrosion pit. Additionally, the points of light can be reflected to appear to be closer or farther apart by different distances based on different sizes of the corrosion pits (e.g., pits having larger aspect ratios can reflect the points of light to appear closer together relative to pits having smaller aspect ratios). The sensor 110 optionally can measure one or more additional features of the corrosion pits, such as volume, depth, width, or the like.

Figure 2:
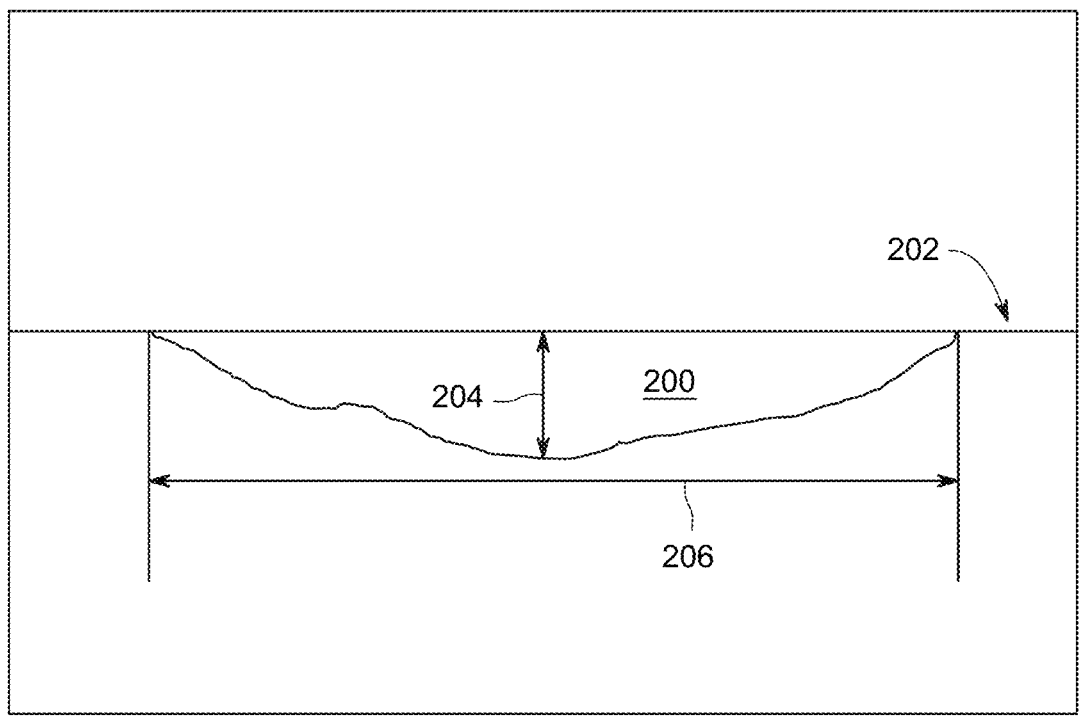
FIG. 2 is a schematic diagram of a corrosion pit and some multi-dimensional characteristics of the corrosion pit.

FIG. 2 illustrates a schematic diagram of a cross-section of a corrosion pit 200 and some multi-dimensional characteristics of the corrosion pit 200. The pit 200 extends into a surface 202 of the equipment 104, such as an outer surface of the equipment 104. The pit 200 can be characterized by several characteristics that represent multi-dimensional information about the corrosion pit 200. These characteristics can include a location of the pit 200 (e.g., the absolute location on the surface 202 of the equipment 104 and/or a location of the pit 200 relative to another pit 200). The characteristics can include a depth measurement 204 that is a distance that the pit 200 extends into the equipment 104 from the surface 202. Another characteristic can include a width measurement 206 that is a distance that the pit 200 extends along one or more directions that are perpendicular to the direction in which the depth 204 is measured. Another characteristic can include an aspect ratio, which is the width 206 of the pit 200 divided by the depth 204 of the pit 200. Another characteristic of the pit 200 can be a volume of the pit 200. Other characteristics of the pit 200 optionally may be measured, such as an area of the pit 200 (e.g., a size or fraction of the area of the surface 202 of the equipment 104 that is replaced by the pit 200 or over which the pit 200 extends), a spacing of the pit 200 (e.g., a distance between the pit 200 and one or more neighboring pits 200), etc.

Figure 3:
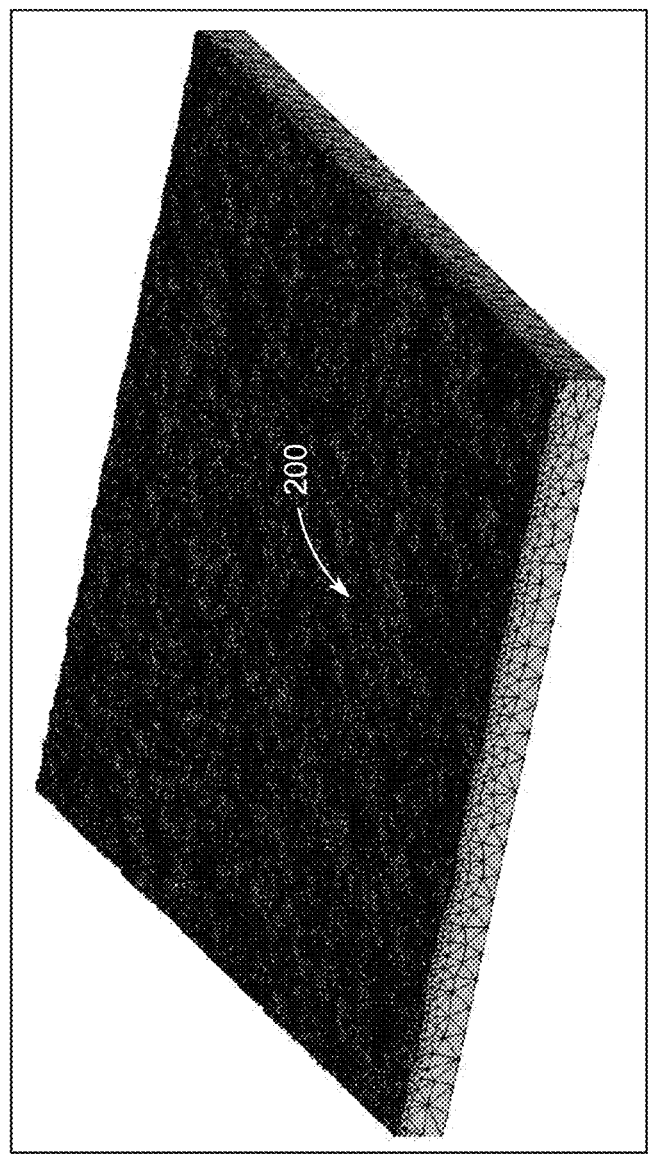
FIG. 3 illustrates one example of a three-dimensional corrosion pit field on equipment.

FIG. 3 illustrates one example of a three-dimensional representation of a corrosion pit field 300 on the equipment 104. The field 300 represents measurements of corrosion pits 200 in the equipment 104. The field 300 can be created by the measurements obtained by the sensor 110. As shown, the field 300 includes pits 200 and other undulations indicative of corrosion of the surface 202 of the equipment 104.

Returning to the description of the system 100 shown in FIG. 1, optionally, the sensor 110 can represent another type of optical sensor or metrology device that provides the characteristics of the corrosion pits 200 in the equipment 104. For example, the sensor 110 can represent an input (e.g., a keyboard, touchscreen, stylus, electronic mouse, antenna, etc.) that is used to provide or receive the characteristics of corrosion pits 200 from a source such as an operator that measured the characteristics. This input can be received via an interface 112 (described below). The pit characteristics can be communicated from the sensor 110 and/or interface to the analysis controller 102, or optionally can be stored in one or more computer readable memories 116, ("Database" in FIG. 1), such as one or more computer hard drives, optical discs, servers, or the like.

The analysis controller 102 also receives operational characteristics of the equipment 104. The interface 112 represents hardware circuitry that includes and/or is connected with one or more communication devices, such as transceiving circuitry, modems, antennas, or the like. The interface 112 receives one or more operational characteristics of the equipment 104 from the equipment controller 108. For example, the operational characteristics can be communicated via one or more wired and/or wireless connections between the equipment controller 108 and the interface 112. The interface 112 can communicate the operational characteristics to the analysis controller 102 and/or the database 116. The analysis controller 102 can obtain the pit characteristics and/or the operational characteristics from the database 116.

The operational characteristics can include engine operating parameters, such as throttle settings and/or how long one or more throttle settings were used. The operational characteristics can include routes over which the equipment 104 traveled. For example, if the equipment 104 is an engine of an aircraft, the operational characteristics can include flight paths, location pairs (e.g., the starting and ending locations for trips of the aircraft), or the like. Another example of the operational characteristics includes environmental exposure, such as temperatures at which the equipment 104 operated, how long the equipment 104 operated at one or more of the temperatures, ambient temperatures to which the equipment 104 was exposed, how long the equipment 104 operated at one or more of the ambient temperatures, humidity to which the equipment 104 was exposed, how long the equipment 104 was exposed to the humidity, the amount of dust or other contaminants to which the equipment 104 was exposed, etc. In one embodiment, the environmental exposure or one or more of the operational characteristics can be provided from one or more equipment sensors 118. The equipment sensor 118 can include a thermocouple or other temperature sensitive device that measures operating temperatures of the equipment 104 and/or ambient temperatures, a hydrometer that measures humidity, a dust sensor that measures amounts of dust or other contaminants to which the equipment 104 was exposed, or the like.

The analysis controller 102 receives one or more of the corrosion pit characteristics and one or more of the operational characteristics of the equipment 104, and performs a stress analysis of the equipment 104 based on the received characteristic(s) at the relevant operating conditions, such as engine operating speeds, temperatures, etc. The analysis controller 102 can use the corrosion characteristics to determine a stress distribution in the equipment 104 in the presence of corrosion pits 200. The analysis controller 102 can perform a finite element analysis stress analysis to identify stress concentrations (e.g., locations or areas of the equipment 104 having stress above a designated threshold) on the surface of the equipment 104.

Figure 4:
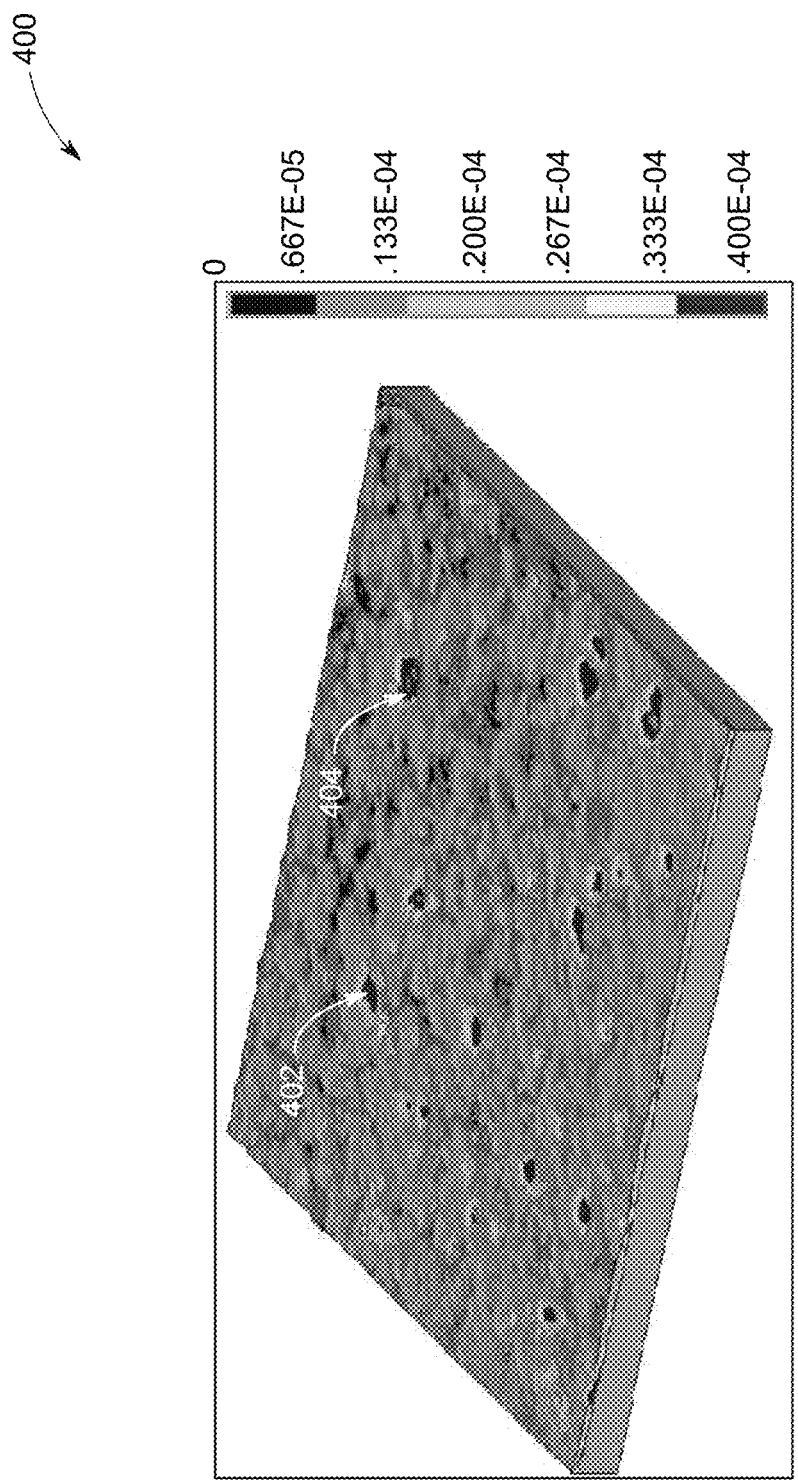
FIG. 4 illustrates one example of a stress field of a portion of the surface of the equipment.

FIG. 4 illustrates one example of a stress field 400 of a portion of the surface 202 of the equipment 104. The stress field 400 represents different stresses on the surface 202 of the equipment 104 that are calculated by the analysis controller 102 for different locations on the equipment 104. The stresses are calculated using finite element analysis based on the locations of the corrosion pits 202, the pit characteristics, and/or the operational characteristics. Labeled locations 402, 404 indicate areas of the surface 202 of the equipment 104 having increased stress relative to other areas.

In some situations, a full finite element analysis may not be used to determine the stresses. Instead, empirical correlations or reduced order equations could be used to predict the stresses. As more information is obtained regarding corrosion pit fields and their characteristics including pit depth, pit spacing, etc., it may be possible to establish reduced order equations to predict the stresses. Optionally, the stress analysis performed by the analysis controller 102 can include comparing the corrosion pit characteristics and/or operational characteristics with different designated corrosion pit characteristics and/or different designated operational characteristics. The different designated corrosion pit characteristics and/or different designated operational characteristics can be associated with different amounts of stress.

For example, larger volumes of corrosion pits, more corrosion pits, smaller aspect ratios of the corrosion pits, larger surface areas of corrosion pits, deeper corrosion pits, smaller distances between corrosion pits, hotter operating temperatures, longer exposure times of the equipment 104 to the elevated operating temperatures, more humid conditions to which the equipment 104 was exposed, longer exposure times of the equipment 104 to the humid conditions, more dust to which the equipment 104 was exposed, etc., can be associated with greater stresses on the equipment 104 than smaller volumes of corrosion pits, fewer corrosion pits, greater aspect ratios of the corrosion pits, smaller surface areas of corrosion pits, shallower corrosion pits, larger distances between corrosion pits, cooler operating temperatures, shorter exposure times of the equipment 104 to the elevated operating temperatures, less humid conditions to which the equipment 104 was exposed, shorter exposure times of the equipment 104 to the humid conditions, less dust to which the equipment 104 was exposed, etc. The amounts of stress associated with the different characteristics can be stored in the database 116, and can be based on previous measurements of stress on other equipment 104 having the associated characteristics. The analysis controller 102 can determine different stresses for different sections of the equipment 104, such as different areas of the equipment 104. In one embodiment, the analysis controller 102 can determine stresses associated with individual corrosion pits in the equipment 104.

In one embodiment, the analysis controller 102 can determine a stress increase generated by a combined effect of adjacent or neighboring corrosion pits 200 in the surface 202 of the equipment 104. The analysis controller 102 can assess the stress increase from the pit-to-pit interaction, as well as quantify the pit-to-pit interactions in the pit field. For example, corrosion pits 200 that are closer together may be associated with greater stresses or larger increases in stress when compared to corrosion pits 200 that are farther apart. Corrosion pits 200 that are near each other can be associated with greater stresses as the location of these nearby pits 200 can be more likely to be a location where a crack in the material of the equipment 104 is likely to begin than in other locations.

The analysis controller 102 determines a residual life of the equipment 104 using the stress analysis. The residual life optionally can be referred to as a predicted remaining useful service life of the equipment 104, and represents a length of time that the equipment 104 can continue to be used or operate before the corrosion in the surface 202 of the equipment 104 will cause the equipment 104 to fail. The residual life that is determined by the analysis controller 102 can account for the position and/or geometry of the corrosion pits 200, the positions of the pits 200 relative to each other in the corrosion pit field, and the pit-to-pit interactions. For example, different stresses, corrosion pit positions, corrosion pit aspect ratios, corrosion pit volumes, distances between corrosion pits, etc., can be associated with different designated residual lives in the database 116. The analysis controller 102 can select the residual life from among these designated residual lives as the predicted residual life for the equipment 104 by comparing the stress or stresses determined for the equipment 104, the corrosion pit characteristics measured for the equipment 104, etc., with the stresses and corrosion pit characteristics associated with the different residual lives.

The designated residual life having the stress(es) and/or corrosion pit characteristics that match or more closely match the stress(es) and/or corrosion pit characteristics of the equipment 104 (e.g., more closely matches than other designated residual lives) can be selected by the analysis controller 102 as the predicted residual life of the equipment 104. The analysis controller 102 can determine the corrosion pit field characteristics and the stress field analysis during a normal engine overhaul of the equipment 104, or the determination and analysis can be performed on a case-by-case basis.

With knowledge of the corrosion condition of the part, the analysis controller 102 can implement remediation to reduce the effect of further corrosion of the equipment 104. Remediation actions implemented by the analysis controller 102 can include, for example, cleaning the equipment 104 to remove corrosive species, blending the corrosion out of the equipment 104, avoiding city-to-city flight paths of the equipment 104 that involve exposure to dust, modification of operating parameters of the equipment 104 to reduce the maximum upper limits on operating temperatures and stresses of the equipment 104 to reduce the rate of corrosion, or the like. In one embodiment, the analysis controller 102 generates and communicates a control signal to the remediation system 106 responsive to the stresses determined by the analysis controller 102 exceeding a first designated threshold and/or the predicted residual life of the equipment 104 being shorter than a second designated threshold. The remediation system 106 can represent automatic cleaning equipment that automatically sprays a cleaning solution or that otherwise removes a corrosive species (e.g., salt) from the equipment 104 responsive to receiving the control signal from the analysis controller 102.

Optionally, the remediation system 106 can represent a scheduling system or dispatch facility that changes a schedule of a vehicle that includes the equipment 104 to prevent the vehicle and equipment 104 from traveling between locations or to a location that would result in the vehicle and equipment 104 moving through dust. Additionally or alternatively, the remediation system 106 represents a spray device or system that automatically applies one or more coatings to the equipment responsive to receiving the control signal from the analysis controller 102. For example, one or more corrosion mitigation coatings such as paints or cladding can be sprayed onto the equipment.

As another example, the analysis controller 102 can communicate the control signal to the equipment controller 108 to direct the equipment controller 108 to restrict the operational parameters of the equipment 104. For example, the equipment controller 108 may prevent the throttle of the equipment 104 from being increased above a threshold setting (that is less or lower than the maximum upper throttle of the equipment 104) to reduce the operating temperature and corrosion of the equipment 104.

The analysis controller 102 can obtain historical data about the equipment 104 or the history of the remediation actions implemented on the equipment 104, including data obtained during previous corrosion pit 200 measurements of the equipment 104. The analysis controller 102 can use this additional information to determine stresses and/or determine whether to implement one or more remediation actions. For example, the analysis controller 102 can determine that the corrosion characteristics alone do not warrant implementing a remediation action. But, the analysis controller 102 can examine historical measurements of the corrosion characteristics and determine that the corrosion characteristics worsening at a rapid rate, such as when the aspect ratios of the corrosion pits 200 are decreasing by at least a designated rate, the number of corrosion pits 200 increasing at a rate that is faster than a designated rate, the spacing between corrosion pits 200 decreasing at a rate that is faster than a designated rate, etc. Even though the analysis controller 102 may not implement a remedial action due to the recently measured corrosion characteristic(s), the analysis controller 102 may determine that the rate of change in the corrosion characteristic(s) is sufficiently large that a remedial action is to be implemented.

In one embodiment, the analysis controller 102 can predict growth of the corrosion on one or more parts of the equipment 104. This growth can be represented or quantified by a change in one or more corrosion characteristics, such as a 20% increase in depth, width, etc. in corrosion pits, a 20% decrease in the aspect ratio of one or more pits, etc. The analysis controller 102 can obtain or receive (e.g., from a schedule of upcoming travel of a vehicle that includes the equipment 104, from operator input, etc.) forthcoming operational characteristics of the equipment 104. These characteristics can include planned throttle settings, planned horsepower outputs, expected ambient temperatures and/or humidity, and the like, for upcoming operation of the equipment 104. These characteristics can be obtained from scheduled operations of the equipment 104, which may dictate the throttle settings, outputs, and/or routes to be traveled by the equipment 104. The ambient conditions (e.g., temperature and/or humidity) can be obtained by reference to weather forecasts for the routes scheduled to be traveled by the equipment 104. The analysis controller 102 can compare the forthcoming (e.g., expected or planned) operational characteristics with designated operational characteristics. The different designated operational characteristics can be associated with different rates of corrosion growth (e.g., in a memory such as the database 116).

The analysis controller 102 can determine which designated operational characteristics match or are closer to the forthcoming operational characteristics (e.g., closer than one or more other designated operational characteristics). The rate of corrosion growth associated with this or these designated operational characteristics can be identified by the analysis controller 102 as predicted corrosion growth. The analysis controller 102 can then inform an operator (e.g., via an output device such as a display, a speaker, or the like) of the predicted rate of corrosion growth and/or the expected corrosion characteristics after the predicted corrosion growth. The analysis controller 102 optionally can automatically schedule one or more remedial actions to be implemented based on the expected corrosion growth so that the remedial action(s) is implemented before the corrosion growth exceeds one or more thresholds.

Figure 5:
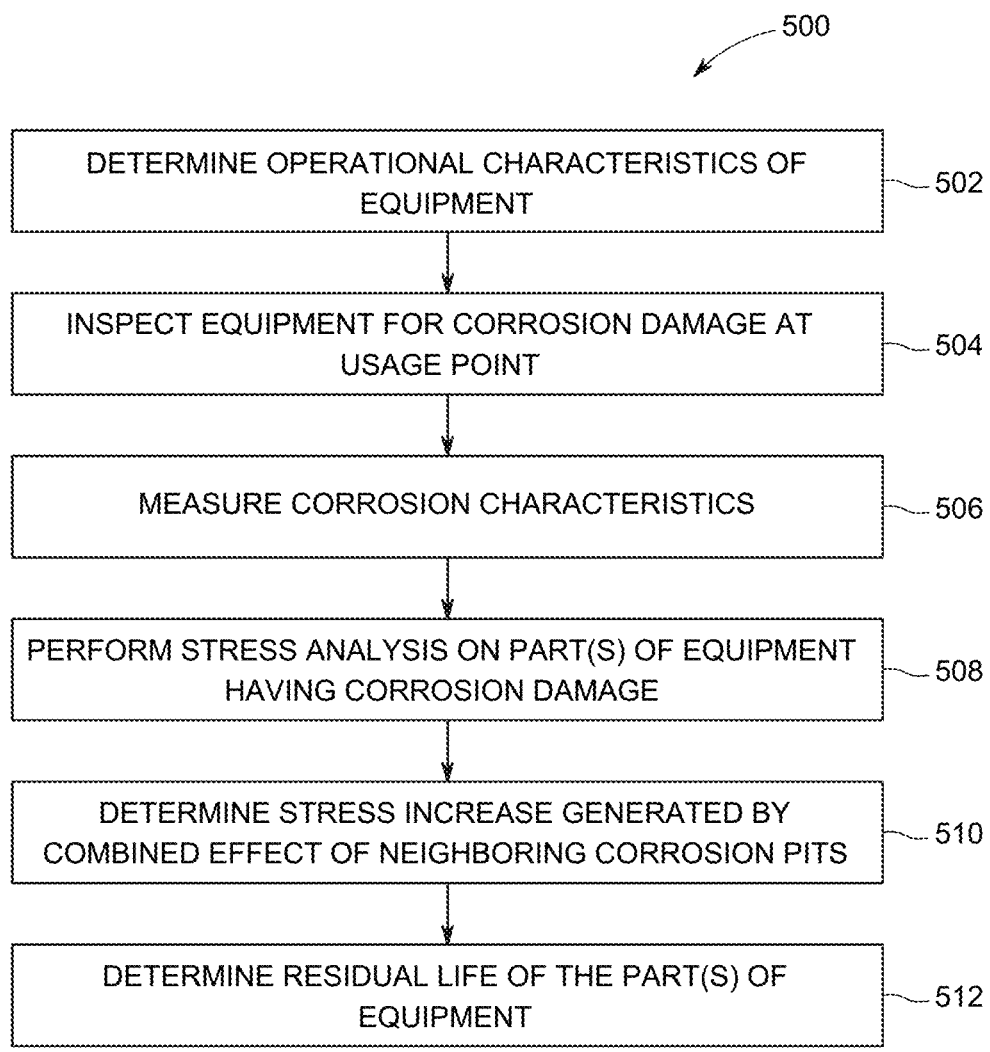
FIG. 5 illustrates a flowchart of a method for monitoring and optionally remediating corrosion in equipment.

FIG. 5 illustrates a flowchart of a method 500 for monitoring and optionally remediating corrosion in equipment. The method 500 can represent some or all the operations performed by the system 100 described above to monitor corrosion in the equipment 104 and optionally implement one or more remedial actions to repair, reduce, or remove corrosion in the equipment 104. At 502, one or more operational characteristics of the equipment 104 are determined. With respect to a turbine engine as the equipment 104, the operational characteristics that are determined can include engine data, such as engine operating parameters, flight routes (including inter-city pairs), and environmental exposure for the flown routes and missions. The level of exposure of the equipment 104 to corrosion damage can be determined as well. This level of exposure can be represented by measurements of the humidity in areas where the equipment 104 operated, how long the equipment was in these areas, temperatures to which the equipment 104 was exposed, how long the equipment 104 was exposed to the temperatures, etc. The operational characteristics can be obtained by the analysis controller 102 from the equipment controller 108, as described above.

At 504, the equipment 104 is inspected for corrosion damage at a usage point. In one embodiment, this inspection is a visual inspection performed by an operator of the equipment 104 or another person. Alternatively, the inspection may be automated by an optical sensor, such as a camera, structured light sensor, or the like. The usage point can be a time during cyclic usage of the equipment 104 where the inspection can occur. For example, the equipment 104 can be inspected when the aircraft that is partially propelled by the equipment 104 is in a designated city, during a regular A-check of the aircraft, during a regular C-check of the aircraft, during regularly scheduled maintenance of the equipment 104, etc.

At 506, one or more characteristics of the corrosion of the equipment 104 are determined. As described above, these corrosion characteristics can be determined by optically measuring various sizes and/or locations of the corrosion pits 200 in one or more parts (e.g., sections) of the equipment 104. The corrosion characteristics can be measured by the corrosion sensor 110.

At 508, a stress analysis is performed for one or more parts of the equipment 104 having corrosion damage. As described above, the stress analysis can be used to calculate stresses on the equipment 104 caused by the corrosion. A finite element analysis (or other stress analysis) can be performed to calculate stresses in the equipment 104 based on the corrosion characteristics and/or operational characteristics, as described above. The effect of the corrosion pits on stresses in the equipment 104 can be determined, and areas where the determined stress indicates a risk of crack initiation can be identified.

At 510, the stress increase generated by neighboring corrosion pits 200 in the equipment 104 can be determined. The stress or stresses calculated at 508 for corrosion pits 200 that are adjacent or neighboring to each other can be examined. Corrosion pits 200 may be adjacent or neighbor each other when no other corrosion pit 200 is disposed between the adjacent or neighboring corrosion pits 200, even if the adjacent or neighboring corrosion pits 200 do not touch or run into each other.

The calculation of one or more of the stresses at 508 may be increased responsive to identifying pit-to-pit interactions. For example, the stress measured for one area of the equipment 104 can be increased if this area includes two or more corrosion pits 200 within a designated distance from each other (e.g., a distance that is less than a width of either of the corrosion pits 200, or another distance). Optionally, a determination is made as to one or more locations or areas on the surface of the equipment 104 having the greatest stress or stress that is greater than one or more other (but not all) other locations or areas on the surface of the equipment 104. This location or area can be identified by determining which corrosion pits 200 are closest together and/or largest relative to other groups or sets of the corrosion pits 200. This location or area can be identified by the analysis controller 102 by examining the corrosion characteristics determined by the corrosion sensor 110.

At 512, the residual life of the equipment 104 (or the part(s) of the equipment 104 for which the corrosion was examined) is determined. Different residual lives can be associated with different stresses determined at 508, 510. Optionally, different residual lives can be associated with identifications of areas or locations having greater stresses due to pit-to-pit interactions. The residual life of the equipment 104 or equipment part(s) can be selected from among these residual lives by determining which residual live(s) have stresses or pit-to-pit interactions that match or more closely match those measured or determined for the equipment 104.

Optionally, one or more remedial actions can be implemented. As described above, depending on the residual life and/or stresses that are determined, one or more remedial actions can be automatically implemented to reduce or remove the corrosion on the equipment 104.

In one embodiment, a system includes an analysis controller configured to determine multi-dimensional characteristics of one or more corrosion pits in equipment and to determine one or more stresses on the equipment based on the characteristics of the corrosion that are determined. The analysis controller also is configured to generate a control signal to implement one or more remedial actions to one or more of remove the one or more corrosion pits, repair the equipment, or restrict operation of the equipment based on the one or more stresses that are determined.

Optionally, the analysis controller is configured to determine the multi-dimensional characteristics of the one or more corrosion pits as an aspect ratio of the one or more corrosion pits, a depth of the one or more corrosion pits, a width of the one or more corrosion pits, a volume of the one or more corrosion pits, or a combination thereof.

Optionally, the analysis controller also is configured to determine a distance between two or more of the corrosion pits. The analysis controller can be configured to determine the one or more stresses based on the multi-dimensional characteristics of the one or more corrosion pits and based on the distance that is determined.

Optionally, the analysis controller is configured to determine one or more operational characteristics of the equipment indicative of usage of the equipment. The analysis controller can be configured to determine the one or more stresses on the equipment also based on the one or more operational characteristics of the equipment.

Optionally, the one or more operational characteristics of the equipment include a throttle setting of the equipment, a horsepower output of the equipment, a temperature of the equipment, an ambient temperature to which the equipment is exposed, a humidity to which the equipment is exposed, or a route over which the equipment travels.

Optionally, the analysis controller is configured to determine the one or more stresses by determining a greater stress on the equipment in a location where two or more of the corrosion pits are closer together in the equipment than in a location where two or more other corrosion pits are farther apart in the equipment.

Optionally, the analysis controller is configured to predict growth of the one or more corrosion pits based on forthcoming operational characteristics of the equipment.

In one embodiment, a method includes optically determining multi-dimensional characteristics of one or more corrosion pits in equipment, determining one or more stresses on the equipment based on the multi-dimensional characteristics of the one or more corrosion pits that are determined, and implementing one or more remedial actions to one or more of remove the one or more corrosion pits, repair the equipment, or restrict operation of the equipment based on the one or more stresses that are determined.

Optionally, optically determining the multi-dimensional characteristics of the one or more corrosion pits includes optically measuring an aspect ratio of the one or more corrosion pits, a depth of the one or more corrosion pits, a width of the one or more corrosion pits, a volume of the one or more corrosion pits, or a combination thereof.

Optionally, the method also includes determining a distance between two or more corrosion pits, where the one or more stresses are determined based on the characteristics of the one or more corrosion pits and based on the distance that is determined.

Optionally, the method also includes determining one or more operational characteristics of the equipment indicative of usage of the equipment, where the one or more stresses on the equipment also are based on the one or more operational characteristics of the equipment.

Optionally, the one or more operational characteristics of the equipment include a throttle setting of the equipment, a horsepower output of the equipment, a temperature of the equipment, an ambient temperature to which the equipment is exposed, a humidity to which the equipment is exposed, or a route over which the equipment travels.

Optionally, determining the one or more stresses includes determining a greater stress on the equipment in a location where two or more corrosion pits are closer together in the equipment than in a location where two or more other corrosion pits are farther apart in the equipment.

Optionally, the method also includes predicting growth of the corrosion based on forthcoming operational characteristics of the equipment.

In one embodiment, a system includes an analysis controller configured to determine one or more multi-dimensional characteristics of corrosion pits in equipment and to determine one or more operational characteristics of the equipment. The analysis controller also is configured to determine one or more stresses on the equipment based on the one or more multi-dimensional characteristics of the corrosion that are determined and based on the one or more operational characteristics. The analysis controller also is configured to generate a control signal to implement one or more remedial actions to one or more of remove the corrosion pits, repair the equipment, or de-rate operation of the equipment based on the one or more stresses that are determined.

Optionally, the analysis controller is configured to determine the one or more multi-dimensional characteristics of the corrosion pits as one or more of an aspect ratio of the corrosion pits, a depth of the corrosion pits, a width of the corrosion pits, or a volume of the corrosion pits.

Optionally, the analysis controller also is configured to determine a distance between two or more of the corrosion pits. The analysis controller can be configured to determine the one or more stresses based on the multi-dimensional characteristics of the corrosion pits and based on the distance that is determined.

Optionally, the one or more operational characteristics of the equipment include a throttle setting of the equipment, a horsepower output of the equipment, a temperature of the equipment, an ambient temperature to which the equipment is exposed, a humidity to which the equipment is exposed, or a route over which the equipment travels.

Optionally, the analysis controller is configured to determine the one or more stresses by determining a greater stress on the equipment in a location where two or more of the corrosion pits are closer together in the equipment than in a location where two or more other pits of the corrosion pits are farther apart in the equipment.

Optionally, the analysis controller is configured to predict growth of the corrosion pits based on forthcoming operational characteristics of the equipment.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
    an optical sensor configured to optically measure multi-dimensional characteristics of one or more corrosion pits in a turbine engine; and
    an analysis controller configured to receive the multi-dimensional characteristics and to determine one or more of an aspect ratio or a volume of the one or more corrosion pits, the analysis controller also configured to determine one or more prior operational characteristics of the turbine engine that are indicative of usage of the turbine engine,
    the analysis controller also configured to determine one or more stresses on the turbine engine based on the one or more of the aspect ratio or the volume that are determined and based on the one or more prior operational characteristics, the one or more prior operational characteristics of the turbine engine include one or more of a throttle setting of the turbine engine, a horsepower output of the turbine engine, a humidity to which the turbine engine is exposed, or a route over which the turbine engine moved,
    the analysis controller configured to predict growth of the one or more corrosion pits based on forthcoming operational characteristics of the turbine engine, wherein different amounts of predicted corrosion growth are associated with different values of the forthcoming operational characteristics,
    wherein the analysis controller also is configured to generate a control signal to remove the one or more corrosion pits, repair the turbine engine, or restrict operation of the turbine engine based on the one or more stresses that are determined and based on the growth of the one or more corrosion pits that is predicted.

2. The system of claim 1, wherein the optical sensor also is configured to measure one or more of a depth or a width of the one or more corrosion pits, and
    wherein the analysis controller is configured to determine the one or more stresses based also on the one or more of the depth or the width of the one or more corrosion pits.

3. The system of claim 1, wherein the optical sensor also is configured to measure a distance between two or more of the corrosion pits, wherein the analysis controller is configured to determine the one or more stresses based also on the distance that is measured.

4. The system of claim 1, wherein the one or more prior operational characteristics of the turbine engine also include one or more of a temperature of the turbine engine or an ambient temperature to which the turbine engine is exposed.

5. The system of claim 1, wherein the analysis controller is configured to determine the one or more stresses by determining a greater stress on the turbine engine in a location where two or more of the corrosion pits are closer together in the turbine engine than in a location where two or more other corrosion pits are farther apart in the turbine engine.

6. The system of claim 1, wherein the analysis controller is configured to predict the growth of the one or more corrosion pits based on one or more of planned throttle settings, planned horsepower outputs, expected ambient temperatures, or expected humidity for upcoming operation of the turbine engine as the forthcoming operational characteristics of the turbine engine.

7. A method comprising:
    optically measuring multi-dimensional characteristics of one or more corrosion pits in a turbine engine using an optical sensor;
    determining one or more of an aspect ratio or a volume of the one or more corrosion pits based on the multi-dimensional characteristics that are measured;
    determining one or more prior operational characteristics of the turbine engine that are indicative of usage of the turbine engine, the one or more prior operational characteristics of the turbine engine include one or more of a throttle setting of the turbine engine, a horsepower output of the turbine engine, a humidity to which the turbine engine is exposed, or a route over which the turbine engine moved;

determining one or more stresses on the turbine engine based on the one or more of the aspect ratio or the volume of the one or more corrosion pits and based on the one or more prior operational characteristics;

predicting growth of the one or more corrosion pits based on forthcoming operational characteristics of the turbine engine, wherein different amounts of predicted corrosion growth are associated with different values of the forthcoming operational characteristics; and one or more of removing the one or more corrosion pits, repairing the turbine engine, or restricting operation of the turbine engine based on the one or more stresses that are determined and based on the growth of the one or more corrosion pits that is predicted.

8. The method of claim 7, further comprising:
optically measuring one or more of a depth of the one or more corrosion pits or a width of the one or more corrosion pits.

9. The method of claim 7, further comprising:
optically measuring a distance between two or more corrosion pits, wherein the one or more stresses are determined based also on the distance that is measured.

10. The method of claim 7, wherein the one or more prior operational characteristics of the turbine engine also include one or more of a temperature of the turbine engine or an ambient temperature to which the turbine engine is exposed.

11. The method of claim 7, wherein determining the one or more stresses includes determining a greater stress on the turbine engine in a location where two or more corrosion pits are closer together in the turbine engine than in a location where two or more other corrosion pits are farther apart in the turbine engine.

12. The method of claim 7, wherein the growth of the corrosion is predicted based on one or more of planned throttle settings, planned horsepower outputs, expected ambient temperatures, or expected humidity for upcoming operation of the turbine engine as the forthcoming operational characteristics of the turbine engine.

13. A system comprising:
an analysis controller configured to receive one or more multi-dimensional characteristics of corrosion pits in equipment from an optical sensor, the analysis controller also configured to determine one or more operational characteristics of the equipment, the one or more operational characteristics including one or more of a throttle setting of the equipment or a horsepower output of the equipment, the analysis controller also configured to determine one or more stresses on the equipment based on the one or more multi-dimensional characteristics of the corrosion that are determined and based on the one or more operational characteristics, wherein the analysis controller also is configured to generate a control signal to one or more of remove the corrosion pits, repair the equipment, or de-rate operation of the equipment based on the one or more stresses that are determined.

14. The system of claim 13, wherein the analysis controller is configured to determine the one or more multi-dimensional characteristics of the corrosion pits as one or more of an aspect ratio of the corrosion pits, a depth of the corrosion pits, a width of the corrosion pits, or a volume of the corrosion pits.

15. The system of claim 13, wherein the analysis controller also is configured to determine a distance between two or more of the corrosion pits, wherein the analysis controller is configured to determine the one or more stresses based on the multi-dimensional characteristics of the corrosion pits and based on the distance that is determined.

16. The system of claim 13, wherein the one or more operational characteristics of the equipment also include an ambient temperature to which the equipment is exposed, a humidity to which the equipment is exposed, or a route over which the equipment propelled an aircraft.

17. The system of claim 13, wherein the analysis controller is configured to determine the one or more stresses by determining a greater stress on the equipment in a location where two or more of the corrosion pits are closer together in the equipment than in a location where two or more other pits of the corrosion pits are farther apart in the equipment.

18. The system of claim 13, wherein the analysis controller is configured to predict growth of the corrosion pits based on forthcoming operational characteristics of the equipment.

19. The system of claim 13, wherein the one or more operational characteristics are prior operational characteristics of the equipment, the analysis controller also configured to determine one or more planned operational characteristics of the equipment for upcoming operation of the equipment, the analysis controller configured to predict growth of the corrosion pits based on one or more planned operational characteristics.

20. The system of claim 19, wherein the analysis controller also is configured to generate the control signal also based the growth of the corrosion pits that is predicted.

* * * * *